(12) United States Patent
Keller et al.

(10) Patent No.: US 9,138,323 B2
(45) Date of Patent: Sep. 22, 2015

(54) FINGER JOINT PROSTHESIS

(75) Inventors: Arnold Keller, Kayhude (DE); Christoph Ranft, Kiel (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 837 days.

(21) Appl. No.: 12/441,817

(22) PCT Filed: Feb. 21, 2008

(86) PCT No.: PCT/EP2008/001359
§ 371 (c)(1),
(2), (4) Date: Nov. 20, 2009

(87) PCT Pub. No.: WO2008/101696
PCT Pub. Date: Aug. 28, 2008

(65) Prior Publication Data
US 2010/0082112 A1  Apr. 1, 2010

(30) Foreign Application Priority Data
Feb. 21, 2007  (DE) .......................... 10 2007 008 406

(51) Int. Cl.
*A61F 2/42* (2006.01)
*A61F 2/30* (2006.01)

(52) U.S. Cl.
CPC ..... *A61F 2/4241* (2013.01); *A61F 2002/30578* (2013.01); *A61F 2002/30624* (2013.01);
(Continued)

(58) Field of Classification Search
CPC ...... A61F 2002/4243–2002/4248; A61F 2/42; A61F 2/4241
USPC .......... 623/20.11–20.13, 21.11, 21.15–21.17, 623/21.19
See application file for complete search history.

(56) References Cited

U.S. PATENT DOCUMENTS 4,193,139 A * 3/1980 Walker ........................ 623/21.17
5,007,932 A * 4/1991 Bekki et al. ................ 623/23.39
(Continued)

FOREIGN PATENT DOCUMENTS

DE      69002159 T2   10/1993
EP      0214773 A2    3/1987
(Continued)

OTHER PUBLICATIONS

Translation of ES2209489T3.*
(Continued)

*Primary Examiner* — Thomas J Sweet
*Assistant Examiner* — Megan Wolf
(74) *Attorney, Agent, or Firm* — Panitch Schwarze Belisario & Nadel LLP

(57) ABSTRACT

A finger joint prosthesis is provided including a joint body having first and second joint elements, which are connected together pivotably about a rotary axis and from each of which extends an anchoring bar for fixing to a proximal and/or distal phalanx. The anchoring bars have eyes with openings for receiving fixing screws. To increase stability, it is proposed that the first joint element have an external hollow body with an insertion opening, that the second joint element have an internal hollow body, and that the internal hollow body in the position of installation can be inserted by way of the insertion opening relatively movably into the external hollow body. A spindle can be inserted in the position of installation into the internal hollow body for rotationally movable connection to the external hollow body.

14 Claims, 1 Drawing Sheet

(52) U.S. Cl.
CPC .............. *A61F2002/4248* (2013.01); *A61F 2310/00023* (2013.01); *A61F 2310/00323* (2013.01); *A61F 2310/00796* (2013.01)

(56) References Cited

U.S. PATENT DOCUMENTS

| | | | |
|---|---|---|---|
| 5,133,761 A | | 7/1992 | Krouskop |
| 5,405,401 A | * | 4/1995 | Lippincott et al. .......... 623/21.15 |
| 5,443,516 A | | 8/1995 | Albrektsson et al. |
| 5,458,647 A | * | 10/1995 | Brochier et al. ............ 623/21.17 |
| 5,984,970 A | * | 11/1999 | Bramlet ...................... 623/21.15 |
| 6,099,571 A | * | 8/2000 | Knapp ....................... 623/21.16 |
| 6,386,877 B1 | * | 5/2002 | Sutter ........................... 433/173 |

FOREIGN PATENT DOCUMENTS

| | | | | |
|---|---|---|---|---|
| EP | 1096906 | B1 | 10/2003 | |
| ES | 2209489 | T3 * | 6/2004 | ............... A61F 2/42 |
| FR | 2843016 | A1 * | 2/2004 | |
| WO | 9011739 | A1 | 10/1990 | |
| WO | 00/01327 | A2 | 1/2000 | |
| WO | 00/04850 | A1 | 2/2000 | |

OTHER PUBLICATIONS

Translation of FR2843016A1 retrieved from espacenet on Feb. 5, 2015.*

* cited by examiner

FINGER JOINT PROSTHESIS

CROSS-REFERENCE TO RELATED APPLICATIONS

This application is a Section 371 of International Application No. PCT/EP2008/001359, filed Feb. 21, 2008, which was published in the English language on Aug. 28, 2008, under International Publication No. WO 2008/101696 A2 and the disclosure of which is incorporated herein by reference.

BACKGROUND OF THE INVENTION

The invention concerns a finger joint prosthesis comprising a joint body having first and second joint elements. The joint elements are connected together pivotably about a rotary axis, and extending from each joint element is an elongate anchoring bar for fixing to a proximal and/or distal phalanx. One or more eyes with openings for receiving fixing screws are also provided on the anchoring bars.

Functional troubles with finger middle joints can occur on the one hand by virtue of genetic degenerative disease, joint arthrosis. In that case, the disease leads to "wear" of the joint cartilage and consequently corresponding inappropriate strains and pressures with complete changes in the joint surfaces, which result in painful restriction on or even elimination of the joint function. On the other hand, functional troubles with the finger middle joints can, however, also occur as a result of an injury, for example due to luxation of the joint or due to a joint fracture. Primary treatment of a joint fracture generally results in what is referred to as "post-traumatic arthrosis" of the joint, which also leads to a painful restriction in function or elimination of function of the finger middle joint.

One way of eliminating the above-indicated functional problems is to stiffen the joint in a position which is convenient for function thereof. That procedure admittedly results in freedom from pain, but it signifies complete functional inoperability of the joint.

For the implantation of earlier finger joint prostheses, the internal lateral ligament at the finger joint had to be released for ulnar access. The joint was then luxated laterally and a part of the palmar plate detached. The head of the first phalanx and the base of the second phalanx were then resized, so that a previously agreed spacing was afforded between the two phalanges. Thereupon a rectangular space extending along a central axis was reamed by a rasp in each phalanx. A shaft, guide was cemented into that rectangular space. The joint elements were then individually fitted with their anchoring bars into the shaft guide, the phalanges were bent back, and the first and second joint elements were hingedly connected together by inserting a spindle into the aligned openings.

As the finger middle joint had to be luxated laterally in the procedure for implantation of the known finger joint prostheses, the extensor tendon system, the two flexor tendons and the lateral ligaments of the joint were irritated, which resulted in operability being later adversely affected. In addition a large amount of bone substance was sacrificed for implantation of the finger joint prosthesis, as a shaft guide had to be inserted in the direction of the central axis of the finger joints.

A markedly improved finger joint prosthesis is known from European Patent EP 1 096 906 to the inventor Christoph Ranft. That permits a novel and improved method while avoiding the above-indicated disadvantages. In the method described in EP 1 096 906 the finger joint prosthesis could be implanted in the assembled condition radially into a previously produced bore in the finger joint, which represents a marked simplification in installation and results in slight injuries to the finger.

On the other hand, that finger joint prosthesis is of an excessively filigree structure and suffers from a lack of strength and durability.

BRIEF SUMMARY OF THE INVENTION

The object of the invention is accordingly to further develop a finger joint prosthesis as set forth in the Background section of this specification, in such a way that the aforementioned disadvantages are at least partially avoided, the finger joint prosthesis has a higher level of stability, but at the same time it can still be easily implanted with slight injury to the patient.

That object is attained in that the first joint element has an external hollow body with an insertion opening, the second joint element has an internal hollow body, the internal hollow body in the position of installation can be inserted by way of the insertion opening relatively movably into the external hollow body, and a spindle can be inserted in the position of installation into the internal hollow body for rotationally movable connection to the external hollow body. Both the external hollow body and also the internal hollow body are respectively provided with an external peripheral surface and an internal peripheral surface. The external peripheral surface of the internal hollow body is slightly smaller than the internal peripheral surface of the external hollow body, so that the internal hollow body can be inserted in the position of installation relatively movably into the external hollow body. Both the external hollow body and also the internal hollow body are of a rotationally symmetrical configuration and are of the same geometry in order to ensure trouble-free rotation. The structures in the form of hollow bodies, which are relatively movable with respect to each other and which slide one within the other, afford the advantage of considerably increased geometrical moments of inertia in relation to torsion and flexing, over the arrangement disclosed in EP 1 096 906 and in which, in particular, torsional forces are carried exclusively by the central spindle.

In a particularly preferred embodiment the external hollow body and the internal hollow body are in the form of hollow cylinders.

It has proven to be particularly advantageous for the external hollow body and the internal hollow body to be made from metal, as metal has a high level of stability and fatigue strength for use in vivo. In that respect, titanium has particularly good sliding and frictional properties. Titanium nitrite, which is biocompatible and has a particularly good abrasion wear property, is particularly preferably used.

If the hollow bodies are made from metal, the spindle can be made from plastic material as that forms a particularly good material pairing with hollow bodies. The use of polyethylene (PE) is particularly preferred. It is, however, also in accordance with an embodiment of the invention for the spindle also to be made from a metal.

To reduce the frictional forces between the ends of the internal hollow body and the external hollow body, plastic discs or washers can be fitted between the end faces of the internal hollow body and the external hollow body, such discs preferably also comprising PE.

The finger joint prosthesis according to one embodiment of the invention can preferably be used for a PIP joint and can carry the forces occurring at that joint without any problem. To provide for the desired force-carrying capability, the outside diameter of the external hollow body is about 1.5 to 2 times as great as the outside diameter of the spindle. In the case of a PIP joint the external hollow body is preferably of an outside diameter of 12 mm and the spindle is of an outside diameter of 6 mm. Use as a replacement for a DIP or MCP joint, however, is also within the scope of embodiments of the invention. In principle, the structures according to the invention can also be embodied for other joints with suitably different dimensioning, while maintaining the above-described advantageous size relationships.

Abutments can be provided between the external hollow body and the internal hollow body, which limit the angle of rotation to a predetermined amount. In a particularly preferred embodiment the abutments are in the form of steps at the outer peripheral surface of the internal hollow body, which in the installation position bear against the edges of the insertion opening of the external hollow body. Preferably, the angle of rotation is 0 to 135 degrees, particularly preferably 0 to 90 degrees.

A further way of attaining the object of the invention provides that the anchoring bar has at least one peg-shaped enlargement portion. Preferably, the enlargement portion extends parallel to the direction of the axis, that is, transversely with respect to the longitudinal direction of the anchoring bar. Besides a slot for the anchoring bar, a corresponding recess must be provided in the corticalis for that enlargement portion. The at least one peg-shaped enlargement portion on the anchoring bar acts as a support for supporting the finger joint prosthesis, in the event of loadings transversely with respect to the longitudinal direction of the anchoring bar, and thus in the longitudinal direction of the joint body.

It is also possible to provide on the anchoring bar a plurality of peg-shaped enlargement portions, which are spaced from each other by openings along the longitudinal axis of the anchoring bar. In plan view those enlargement portions can essentially involve the geometry of a W, a U or a V. Those enlargement portions are preferably arranged in displaced relationship from the eyes on the anchoring bar, in order not to impede screwing the fixing screws into the finger joint bone and also to permit the fixing screws to be screwed in an inclined manner. For that purpose, bevels can also be provided on the anchoring bar.

Preferably, the peg-shaped enlargement portions are provided at the front side of the anchoring bars, which in the installation position is towards the finger joint bone.

For carrying forces which act on the anchoring bars, it has proven to be particularly desirable if at least one enlargement portion is provided at the outer free end of the anchoring bars and a further one at the connecting region of the anchoring bar to the hollow body.

A further increase in the contact surface area within the finger joint bone can be achieved if, in addition or alternatively, an enlargement portion is provided on the front side of the anchoring bar, that is remote from the finger joint bone.

The enlargement portion of the front side and/or the rear side of the anchoring bar—in plan view—is in the configuration of a V or a W, wherein the somewhat longer proximal anchoring bar is preferably in the configuration of a W and the somewhat shorter distal anchoring bar is preferably in the configuration of a V.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
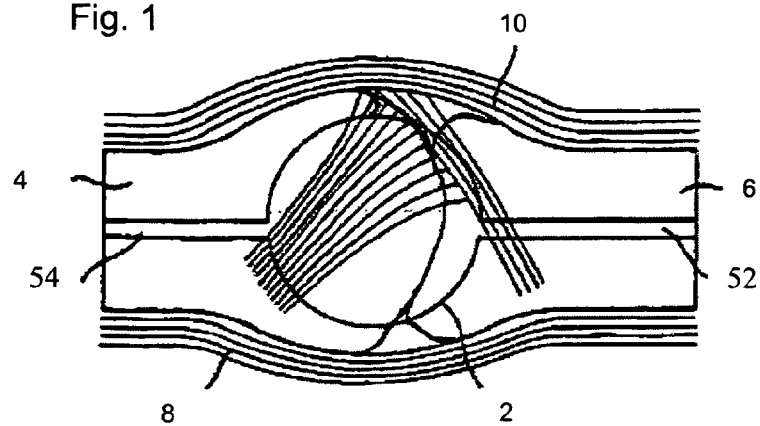
FIG. 1 is a diagrammatic radial view of a finger middle joint, the location for implantation of a finger joint prosthesis being indicated.

FIG. 1 shows the radial side of a finger middle joint 2 with the proximal phalanx 4, that is which is towards the body, and the distal phalanx 6, that is which is remote from the body. The extensor tendon 8 is shown underneath the phalanx and the flexor tendon 10 is shown above the middle phalanx.

Figure 2:
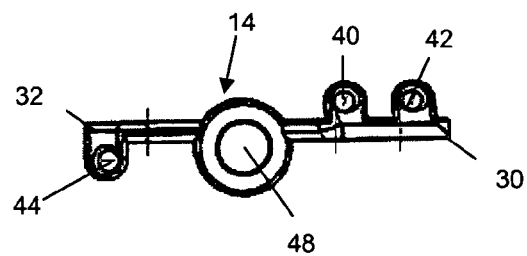
FIG. 2 is a front view of a finger joint prosthesis according to an embodiment of the invention.
Figure 3:
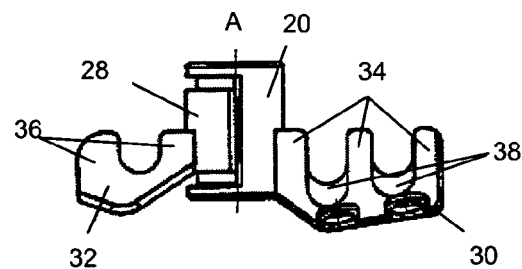
FIG. 3 is a plan view of the finger joint prosthesis of FIG. 2.
Figure 4:
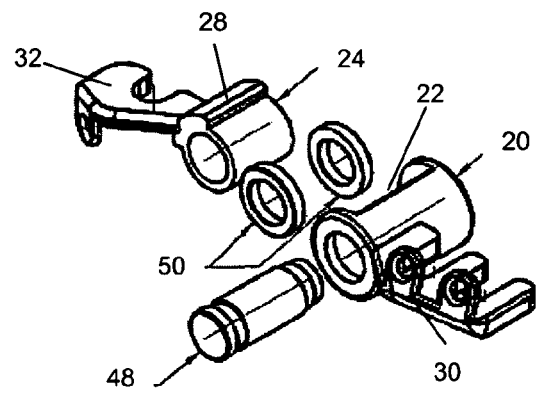
FIG. 4 is a exploded perspective view of the finger joint prosthesis of FIGS. 2 and 3.

The finger joint prosthesis shown in FIGS. 2 to 4 serves for radial implantation in the finger joint shown in FIG. 1 at the location of the hinge joint which is indicated in FIG. 1 by the circle at the center.

FIG. 2 shows a side view of the assembled finger joint prosthesis. It comprises a joint body 14 including a first joint element and a second joint element, which are hingedly connected in such a way that the second joint element is pivotable with respect to the first joint element about a vertical axis A shown in FIG. 3.

FIGS. 2 and 3 show a side view and a plan view of the finger joint prosthesis in the implantation position. As best seen in the exploded view of FIG. 4, the first joint element includes an external hollow cylinder 20 which has an insertion opening 22 at one side of the axis A. The internal hollow cylinder 24 of the second joint element can be rotationally movably inserted into that insertion opening 22 of the external hollow cylinder 20, which extends over half the peripheral surface of the cylinder 24. Formed externally on the internal hollow cylinder 24 of the second joint element is an abutment 28 which extends approximately over an angular portion of 90° and which forms the abutment edges of the internal hollow cylinder 24, for abutting against the inside edges of the insertion opening 22 of the external hollow cylinder 20. The displaceable angular range can be adjusted as desired by virtue of a suitable configuration of the abutment 28.

A proximally extending, areal, proximal anchoring bar 30 is formed in one piece at one side on the outside peripheral surface of the external hollow cylinder 20. That proximal anchoring bar 30 extends from the rear side of the external hollow cylinder 20 approximately to the center thereof. The proximal anchoring bar 30 provides a surface which extends transversely with respect to the axis A of the joint body 14. The height of the proximal anchoring bar is about one-quarter of the total length of the joint body 14. As can be seen from FIG. 2 the proximal anchoring bar 30 is formed on the outside peripheral surface of the external hollow cylinder 20 somewhat above a notional horizontal plane extending through the center point of the axis.

In the implantation position shown in FIG. 2, a distal anchoring bar 32, which extends from the rear side to approximately the center of the abutment 28, is formed in one piece on the internal hollow cylinder 24 in a plane with the proximal anchoring bar 30. The distal anchoring bar 32 extends distally outwardly from the internal hollow cylinder 24 and is also of an areal nature.

The proximal anchoring bar 30 and the distal anchoring bar 32 each have leg-shaped enlargement portions 34, 36 on their front side, which is towards the bone in the installation position. Those enlargement portions 34, 36 extend forwardly transversely with respect to the longitudinal direction of the anchoring bars 30, 32 over a length of approximately half the joint body 14. At least one enlargement portion 34, 36 is provided at the outer free end of the anchoring bars 30, 32, in order here to carry forces acting on the anchoring bars 30, 32.

The distal anchoring bar 30 can be pivoted out of the implantation position shown in the Figures upwardly through about 90 degrees in relation to the proximal anchoring bar 32.

A first fixing eye 40 is integrally formed on the top side of the proximal anchoring bar 30 in adjoining and slightly inwardly displaced relationship from the outer free end of the proximal anchoring bar 30. A second fixing eye 42 of a geometrically identical configuration is integrally formed at a spacing displaced radially inwardly in the direction of the external hollow cylinder 20 on the proximal anchoring bar 30. The first fixing eye 40 and the second fixing eye 42 are so arranged on the proximal anchoring bar 30 that they are disposed precisely in the region of openings between the mutually spaced, leg-shaped enlargement portions 34, 36, in order to permit the fixing screws to be screwed into the openings in the fixing eyes 40, 42, which extend substantially parallel to the central axis of the joint body 14. In order to permit the fixing screws to be screwed in an inclined manner into the fixing eyes 40, 42, bevels 38 are provided on the anchoring bars 30, 32 in the region of the fixing eyes 40, 42 at the apex points of the openings between the enlargement portions 34, 36. The material thickness increases from the front end in the direction of the rear side, to the full material thickness of the anchoring bar of 0.7 to 1.3 mm. The fixing eyes 40, 42 can also be inclined out of the vertical through about 5 to 10 degrees in order to assist with screwing in the fixing screws in an inclined manner.

In plan view the proximal anchoring bar is substantially of the geometry of a W.

The rear side (remote from the bone in the installation position) of the proximal anchoring bar 30 extends from the rear side of the external hollow cylinder 20 at an angle of about 45° rearwardly to an apex point and rises therefrom to the outer free end at a shallow angle. The limbs, formed in that way, of the anchoring bars 30, 32 include between them an obtuse angle, which is preferably 150 to 170 degrees, in order thereby to match the anchoring bars to the natural geometry of the finger bone and to improve the stability by increasing the support contact surface in the bone without restricting the mobility of the joint.

Two enlargement portions 36, which extend substantially parallel to the axis A, are also formed on the distal anchoring bar 32. The enlargement portions 36 are spaced from each other by an operation with a bevel at the apex point. A third fixing eye 44 is integrally formed at the underside of the distal anchoring bar 32 at a position of being displaced slightly outwardly from the opening. The third fixing eye 44 is integrally formed approximately at the apex point of the front limb of the distal anchoring bar 32.

A PE spindle 48 is inserted through an end opening at the front side in the end of the external hollow cylinder 20 for relatively movably connecting the first joint element to the second joint element. The spindle 48 passes through the cylindrical opening in the internal hollow cylinder 24 and thus fixes it in the external hollow cylinder 20. The spindle 48 is captively connected to the external hollow cylinder 20 by virtue of a suitable press fit between the spindle 48 and the external hollow cylinder 20. At the front end the spindle 48 has a pin portion of reduced diameter which can be pressed into the front end face of the external hollow cylinder 20.

To reduce the friction between the outside front ends of the internal hollow cylinder 24, which is made from titanium nitride, and the inside front ends of the external hollow cylinder 20, which is also made from titanium nitride, PE annular discs 50 are inserted.

For implantation of the finger joint prosthesis, after detachment of the corresponding lateral ligament a bore is milled by means of a round milling cutter from the radial side, at the location indicated in FIG. 1 by the central circle. The center point of the bore corresponds to the center point of rotation of the phalanges 4, 6 at the beginning of the pivotal movement of the distal phalanx 6 out of the extended position into the flexed position. The inside diameter and the height of the bore correspond to the outside diameter and the height of the joint body 14. After the bore has been milled, two slots 52, 54, extending in the longitudinal central direction of the phalanges from the milled bore, are milled from the radial side with a slot milling cutter. In that respect the shape of the slots 52, 54 corresponds to the geometry of the anchoring bars 30, 32.

After milling of the bore and milling of the slots 52, 54 the finger joint prostheses are inserted with their front end into the milled bore, in which case the anchoring bars 30, 32 are pushed into the slots 52, 54 until the fixing eyes 40, 42 and 44 bear against the finger bones. Then, the anchoring bars 30, 32 are fixed to the bone material of the corresponding phalanx 4, 6. That is effected by screwing titanium screws through the fixing eyes 40, 42 and 44 into the bone material.

The component parts of the finger joint prosthesis are preferably made from metal, particularly preferably titanium or titanium nitride. That material has the advantage that a durable high level of implant stability is achieved by bone growing into the porous surface of the material. It is further possible for the surface of the material to be provided with a biocompatible coating which promotes bone growth into the surface. For example, hydroxyl apatite is particularly advantageous.

To achieve a suitable anti-friction pairing between the spindle and the hollow bodies, the spindle is preferably made of a material having a degree of hardness different from the material of the hollow bodies, which materials however together form a good anti-friction pairing. When using hollow bodies of titanium or titanium nitride, a spindle of plastic material has proven to be advantageous, in particular a spindle of UHMWPE. It is, however, also possible to consider all further suitable material pairings with suitable sliding properties.

Depending on the size of the finger joint to be replaced, the dimensions of the finger joint prosthesis are preferably in the following ranges:

| | |
|---|---|
| Diameter of the joint body: | 6 to 8 mm |
| Diameter of the spindle: | 3 to 4 mm |
| Length of the anchoring bars: | 4 to 8 mm |
| Thickness of the anchoring bars: | 0.7 to 1.3 mm |

The invention has been described with reference to replacement of the finger middle joint by the finger joint prosthesis according to the invention. In the same manner, the finger joint prosthesis can also be used for replacement of the end joints of the fingers, with suitable adaptation of the dimensions, while retaining the size relationships.

The subject-matter of the present invention involves not only the subject-matter of the individual claims but also the combination of the individual claims with each other. All features and details disclosed in the documents—including the Abstract—, in particular the three-dimensional configurations illustrated in the drawings, are claimed as essential to the invention insofar as they are novel individually or in combination over the state of the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A finger joint prosthesis comprising a joint body having:
    a first joint element pivotally connected to a second joint element about a rotary axis, the first joint element having an external hollow cylindrical body with an insertion opening at one side and the second joint element having an internal hollow cylindrical body, the external hollow cylindrical body and the internal hollow cylindrical body being of a rotationally symmetrical configuration, and each of the external and internal hollow cylindrical bodies having an internal peripheral surface and an external peripheral surface, the external peripheral surface of the internal hollow cylindrical body being slightly smaller than the internal peripheral surface of the external hollow cylindrical body; and
    first and second areal anchoring bars extending distally outwardly from each of the first and second joint elements, respectively, the first and second areal anchoring bars being configured to be fixed to a proximal and a distal phalanx, respectively,
        wherein the first areal anchoring bar is provided on the external peripheral surface of the external hollow cylindrical body at a position opposite the insertion opening and the second areal anchoring bar is provided on the external peripheral surface of the internal hollow cylindrical body,
        wherein each areal anchoring bar defines a plane extending perpendicularly to the rotary axis, each areal anchoring bar being configured to be fixed into planar slots which extend longitudinally relative to the proximal and distal phalanges,
        wherein each areal anchoring bar has a first end including one or more securing eyes extending transversely to the plane thereof and an opposing second end which is free of securing eyes and is configured to be radially inserted into the planar slots, each of the securing eyes including an opening for receiving fixing screws therein,
        wherein in an installation position of the prosthesis, the internal hollow cylindrical body is inserted relatively movably in the external hollow cylindrical body and a spindle is inserted in the internal hollow cylindrical body, the internal hollow cylindrical body being rotationally movable relative to the external hollow cylindrical body,
        wherein the prosthesis is configured to be radially implanted into a bore produced in a finger joint, each of the areal anchoring bars being configured to be radially inserted to the planar slots, and
        wherein at least one of the areal anchoring bars has a plurality of leg-shaped enlargement portions extending parallel to the rotary axis, first ends of the leg-shaped enlargement portions being attached to the areal anchoring bar and opposing second ends of the leg-shaped enlargement portions being separate and spaced apart from each other.

2. The finger joint prosthesis according to claim 1, wherein the external hollow cylindrical body and the internal hollow cylindrical body comprise metal.

3. The finger joint prosthesis according to claim 1, wherein the spindle comprises plastic material.

4. The finger joint prosthesis according to claim 1, further comprising annular discs fitted between the external hollow cylindrical body and the internal hollow cylindrical body at their ends.

5. The finger joint prosthesis according to claim 1, wherein an outside diameter of the external hollow cylindrical body is about 1.5 to 2 times as great as an outside diameter of the spindle.

6. The finger joint prosthesis according to claim 1, further comprising abutments provided between the external hollow cylindrical body and the internal hollow cylindrical body.

7. The finger joint prosthesis according to claim 6, wherein the abutments are provided on the internal hollow cylindrical body.

8. The finger joint prosthesis according to claim 6, wherein the abutments include an angle of about 130°.

9. The finger joint prosthesis according to claim 1, wherein the leg-shaped enlargement portions are provided at a free end of the anchoring bar.

10. The finger joint prosthesis according to claim 1, wherein the second ends of the leg-shaped enlargement portions are spaced from each other by one or more openings along a longitudinal axis of the anchoring bars.

11. The finger joint prosthesis according to claim 1, wherein at least one of the leg-shaped enlargement portions is provided at a front side of the anchoring bars.

12. The finger joint prosthesis according to claim 11, wherein an additional enlargement portion is provided on a rear side of the anchoring bars.

13. The finger joint prosthesis according to claim 12, wherein the enlargement portion on the rear side is adapted to a geometry of the bone.

14. The finger joint prosthesis according to claim 1, wherein the leg-shaped enlargement portions are arranged in a displaced relationship to the securing eyes at the first end of the areal anchoring bar.

* * * * *